United States Patent
Fujinami et al.

(10) Patent No.: US 11,980,524 B2
(45) Date of Patent: May 14, 2024

(54) DENTAL PROSTHESIS AND COMPONENT THEREOF

(71) Applicants: Medical Foundation Natural Smile, Kanagawa (JP); OKABE Co., Ltd., Fukuoka (JP); SofSera Corporation, Tokyo (JP)

(72) Inventors: Jun Fujinami, Kanagawa (JP); Miwa Fujinami, Kanagawa (JP); Shinichi Okabe, Fukuoka (JP); Yohki Hieda, Tokyo (JP); Yasumichi Kogai, Tokyo (JP); Karl Kazushige Kawabe, Tokyo (JP)

(73) Assignees: Medical Foundation Natural Smile, Kanagawa (JP); OKABE Co., Ltd., Fukuoka (JP); SofSera Corporation, Tokyo (JP)

(*) Notice: Subject to any disclaimer, the term of this patent is extended or adjusted under 35 U.S.C. 154(b) by 28 days.

(21) Appl. No.: 17/857,903

(22) Filed: Jul. 5, 2022

(65) Prior Publication Data

US 2022/0331070 A1     Oct. 20, 2022

Related U.S. Application Data

(63) Continuation of application No. 16/096,492, filed as application No. PCT/JP2017/016443 on Apr. 25, 2017, now abandoned.

(30) Foreign Application Priority Data

Apr. 25, 2016   (JP) .................................. 2016-087553

(51) Int. Cl.
 *A61C 8/00*    (2006.01)
 *A61C 13/09*   (2006.01)
 (Continued)

(52) U.S. Cl.
 CPC .............. *A61C 8/0013* (2013.01); *A61C 8/00* (2013.01); *A61K 6/838* (2020.01); *A61L 27/12* (2013.01);
 (Continued)

(58) Field of Classification Search
 CPC .......... A61C 8/005; A61C 8/0012–016; A61C 13/09; A61K 6/33; A61K 6/838; A61L 27/12; A61L 27/40
 See application file for complete search history.

(56) References Cited

U.S. PATENT DOCUMENTS 5,123,844 A * 6/1992 Wakai ..................... A61L 27/32
                                                    433/201.1
5,344,457 A * 9/1994 Pilliar .................... A61L 27/04
                                                    433/175
(Continued)

FOREIGN PATENT DOCUMENTS

JP        2005319022      * 11/2005

*Primary Examiner* — Edward Moran
*Assistant Examiner* — Matthew P Saunders
(74) *Attorney, Agent, or Firm* — Osha Bergman Watanabe & Burton LLP

(57) ABSTRACT

This invention provides a measure that makes it possible to prevent more effectively, in comparison with the prior art, the invasion of germs from the gap between a dental prosthesis and the gingiva when the dental prosthesis is used in an oral cavity as well as the infection and inflammation associated therewith.

There is a dental prosthesis or a component thereof, characterized in that: the dental prosthesis or the component thereof has hydroxyapatite fine particles on a surface of the dental prosthesis or the component thereof; the hydroxyapatite fine particles are sintered bodies; and the hydroxyapatite fine particles have a mean particle size of 10 to 1,000 nm.

9 Claims, 5 Drawing Sheets

(51) Int. Cl.
  *A61K 6/838* (2020.01)
  *A61L 27/12* (2006.01)
  *A61L 27/40* (2006.01)
(52) U.S. Cl.
  CPC .............. *A61L 27/40* (2013.01); *A61C 8/005* (2013.01); *A61C 13/09* (2013.01)

(56) References Cited

U.S. PATENT DOCUMENTS

| | | | | |
|---|---|---|---|---|
| 5,730,598 A | * | 3/1998 | Story | C23C 4/18 427/2.27 |
| 6,283,997 B1 | * | 9/2001 | Garg | A61L 27/446 623/901 |
| 2007/0110890 A1 | * | 5/2007 | Berckmans, III | C23C 30/00 427/2.24 |

* cited by examiner

HEAT-TREATED TITANIUM

SAMPLE MATERIAL ACCORDING TO THE PRESENT EXAMPLE

BEFORE ULTRASONIC IRRADIATION

30 MINUTES AFTER ULTRASONIC IRRADIATION
BINDER IS DROPPED OFF AND SUBSTRATE IS EXPOSED

DENTAL PROSTHESIS AND COMPONENT THEREOF

TECHNICAL FIELD

The present invention relates to a dental prosthesis used in an oral cavity and a component thereof.

BACKGROUND ART

As shown in FIG. 1, an implant 1 (implant kit) is composed of an upper structure 1-1 (dental crown part: implant denture) and an implant body 1-4 {dental root part: fixture (artificial dental root)}. Here, an abutment 1-3 is a part that connects the upper structure 1-1 and the implant body 1-4 via a screw 1-2.

When a long period elapses after the implant was embedded, a gap is formed between the abutment (dental material) and the gingiva, and germs invade through said gap, which may cause infection and inflammation. Accordingly, various methods have been proposed to solve this problem.

First, Patent Literature 1 proposes a technical solution of imparting antibacterial properties to an artificial dental root by coating a gingival abutting surface of the artificial dental root with a bioinert component {$CaMgSi_2O_6$ (diopside) crystal}. In addition, Patent Literature 2 proposes a technical solution of applying an antimicrobial coating to an abutment for forming a surface layer containing gallium oxide. Further, Patent Literature 3 proposes a technical solution of coating an implant surface with calcium phosphate ions containing a positively charged therapeutic agent complex by using an electrolytic solution containing a therapeutic agent+a complexing agent+calcium ions+phosphorus ions. Furthermore, Patent Literature 4 proposes a technical solution of coating a surface of an implant with an NO releasing polymer.

CITATION LIST

Patent Literature

Patent Literature 1: JP H04-183463 A
Patent Literature 2: JP 2015-516829 A
Patent Literature 3: JP 2012-522885 A
Patent Literature 4: JP 2009-507539 A

SUMMARY OF INVENTION

Technical Problem

An object of the present invention is to provide a means (e.g. an abutment) that makes it possible to prevent more effectively, in comparison with the prior art, the invasion of germs from the gap between a dental prosthesis and the gingiva when said dental prosthesis is used in an oral cavity as well as the infection and inflammation associated therewith.

Solution to Problem

[1] A dental prosthesis or a component thereof, wherein the dental prosthesis or the component thereof includes hydroxyapatite fine particles on a surface of the dental prosthesis or the component thereof,
the hydroxyapatite fine particles are sintered bodies, and the hydroxyapatite fine particles have a mean particle size of 10 to 1,000 nm.

[2] The dental prosthesis or the component thereof according to the above [1], wherein the dental prosthesis is an implant that is an artificial dental root to be embedded into a bone in an oral cavity, and the component is an abutment used for the implant.

Advantageous Effects of Invention

According to the present invention, it is possible to provide a means that makes it possible to prevent more effectively the invasion of germs from the gap between a dental prosthesis and the gingiva when said dental prosthesis is used in an oral cavity as well as the infection and inflammation associated therewith. In particular, the means is an abutment.

DESCRIPTION OF EMBODIMENTS

In the following description, an implant will be taken as an example of a dental prosthesis. The dental prosthesis according to the present invention is an artificial object used for the purpose of restoring dysfunction and aesthetics of the stomatognathic system caused by defects in teeth and tissues associated with teeth. Specifically, the dental prosthesis according to the present invention refers to inlays, onlays, crowns, bridges, dentures (complete dentures and partial dentures), artificial teeth, and implants. Hereinafter, an implant (one of its components is an abutment) will be described as an example of a dental prosthesis.

Overall Structure of Implant

Figure 1:
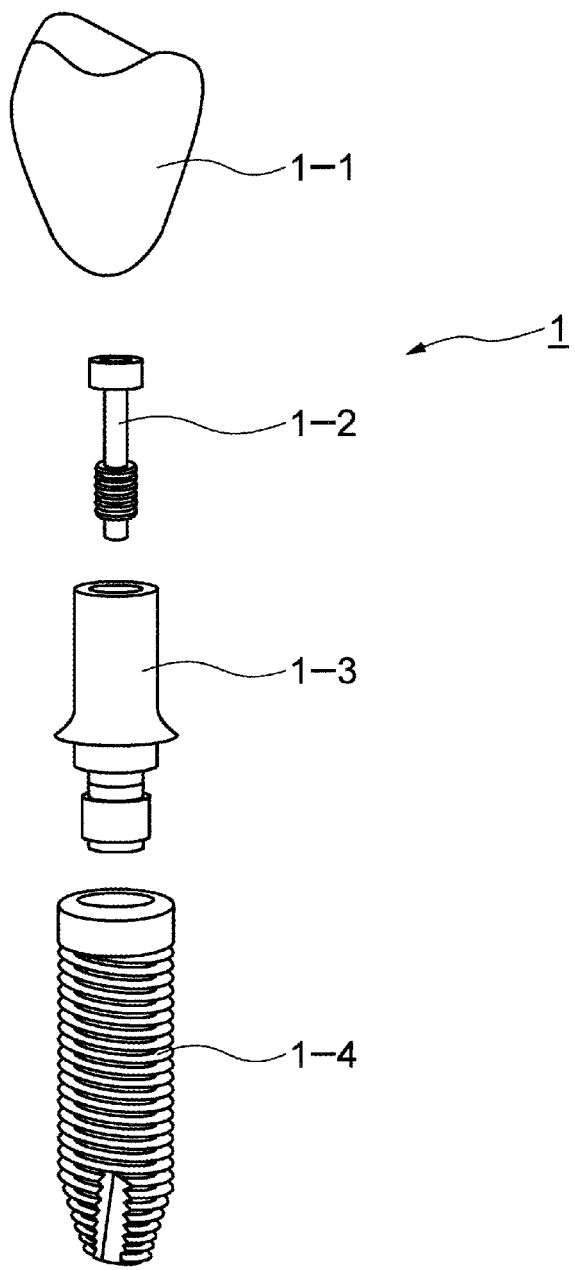
FIG. 1 is an overall configuration diagram of a two-piece type implant.

The implant to which the abutment (dental material) according to the present invention is applied is not particularly limited, and, examples thereof include a connection type implant (two-piece type) in which an "abutment (dental material)" and a "fixture" are separated and an integral type implant (one-piece type) in which an "abutment (dental material)" and a "fixture" are integrated. Hereinafter, the present invention will be described by using a two-piece type as an example, but the present invention also includes a one-piece type. Here, FIG. 1 is an overall configuration diagram of an implant according to a two-piece type. Referring to FIG. 1, the implant 1 is composed of the upper structure 1-1 (dental crown part: implant denture) and the implant body 1-4 {dental root part: fixture (artificial dental root)}. Here, the abutment 1-3 is a part that connects the upper structure 1-1 and the implant body 1-4 via the screw 1-2. Meanwhile, FIG. 1 is merely an example, and the size and shape of each part in the implant to which the abutment (dental material) according to the present invention is applied is not limited to the example of FIG. 1 at all.

Abutment (Dental Material)

Hereinafter, the abutment (dental material) according to the present invention will be described in detail. The abutment (dental material) according to the present invention has hydroxyapatite fine particles on a surface thereof; the hydroxyapatite fine particles are sintered bodies; and the hydroxyapatite fine particles have a mean particle size of 10 to 1,000 nm. Each element will be described in detail below.

Material (Abutment (Dental Material))

The material of the abutment (dental material) is not particularly limited and conventionally known materials can be used. Examples thereof include noble metals, pure titanium, titanium alloys, titanium-nickel alloys, cobalt-chromium alloys, zirconia, artificial sapphire, acrylic acid, acrylic acid derivatives, methacrylic acid, methacrylic acid derivatives, and aromatic polyether ketones.

(Hydroxyapatite Fine Particles)

One feature of the hydroxyapatite fine particles according to the present invention is that the hydroxyapatite fine particles are sintered bodies. Here, the higher the degree of sintering is, the higher the degree of crystallinity is. It is preferable that the sintered hydroxyapatite fine particles according to the present invention are highly crystalline. Specifically, the narrower the half-value width of the peak representing each crystal plane is, the higher the crystallinity is. Here, the "high crystallinity" of the highly crystalline calcium phosphate according to the present invention means that the half-value width at d=2.814 is 0.8 or less (preferably 0.5 or less). Meanwhile, the degree of crystallinity of calcium phosphate can be measured by an X-ray diffraction method (XRD).

Furthermore, the sintered hydroxyapatite fine particles according to the present invention have a mean particle size of 10 to 1,000 nm, preferably 20 to 300 nm, more preferably 20 to 250 nm, especially preferably 20 to 150 nm, further especially preferably 20 to 100 nm, extremely preferably 20 to 80 nm, and the most preferably 25 to 60 nm. By sintering hydroxyapatite and making the sintered hydroxyapatite fine particles have said range of the particle size, (1) the production of fibronectin (adhesive protein) by gingival fibroblasts becomes active, and as a result, gingival fibroblasts bind firmly to the abutment (dental material), and (2) gingival fibroblasts bound to the abutment (dental material) produce collagen. A new finding of this time is that gingival fibroblasts bound to the abutment (dental material) in this way produce collagen "fibrously" (via sintered hydroxyapatite fine particles). A further new finding is that said produced fibrous collagen stretches "fibrously" between the abutment (dental material) and the gingiva, and as a result, gap between the abutment (dental material) and the gingiva are eliminated and the gingiva and the abutment (dental material) are strongly adhered, which makes it possible to prevent the invasion of germs and to prevent infection and inflammation. Meanwhile, the coefficient of variation of the particle sizes is preferably 20% or less, more preferably 18% or less, and further preferably 15% or less. Meanwhile, the mean particle size and the coefficient of variation can be calculated by measuring the particle sizes of at least 100 or more primary particles by using an electron microscope. Meanwhile, the "coefficient of variation" is a value indicating the variation of particle sizes among particles which can be calculated by: standard deviation/mean particle size×100 (%). The shape of the calcium phosphate fine particle is not particularly limited, and may be, for example, particulate (spherical) or rod-like. Meanwhile, in the case where the fine particle is a rod-like shape, the mean particle size is measured by the major axis of said particle.

Examples of the sintered hydroxyapatite fine particles include those disclosed in JP5043436B. In this literature, it is described that sintered hydroxyapatite fine particles having a small particle size can be produced by sintering primary particles of hydroxyapatite after attaching a fusion preventive agent to the primary particles. Ceramics (sintered hydroxyapatite fine particles) disclosed by this literature is sufficiently practical. However, as a result of using a fusion preventive agent at the manufacturing process, calcium carbonate may be present on the surface of the obtained sintered hydroxyapatite fine particles. When calcium carbonate is present on the surface, there is a risk of fluctuation of pH due to difference in solubility or loss of the materials due to dissolution. This is a disadvantage when such sintered hydroxyapatite fine particles are applied in a living body. Accordingly, it is preferable that the sintered hydroxyapatite fine particles are substantially free of calcium carbonate. Examples of such ceramics (sintered hydroxyapatite fine particles) include those disclosed in JP5980982B, JP6072967B, and JP6072968B. These ceramics are extremely advantageous because in a living body, they can reduce the rapid pH change due to dissolution and a risk of inducing inflammation of surrounding tissues accompanied therewith and, in the first place, there is no risk of the loss of the materials due to dissolution at all.

Here, the phrase "free of calcium carbonate" means that the sintered hydroxyapatite fine particles do not substantially contain calcium carbonate, and the phrase does not necessarily exclude the inclusion of a trace amount of calcium carbonate. In particular, the phrase means that the sintered hydroxyapatite fine particles satisfy the following criteria (1) to (3), and preferably further satisfy the criterion (4).

(1) Based on the measurement result of X-ray diffraction, amounts of calcium carbonate is equal to or lower than: calcium carbonate (formula weight: 100.09)/hydroxyapatite (formula weight: 1004.62)=0.1/99.9 (formula weight conversion ratio).

(2) In the thermal gravimetric-differential thermal analysis (TG-DTA) measurement, weight loss of 2% or more with clear endothermic change is not observed at 650° C. to 800° C.

(3) In the chart showing the absorbance calculated from the spectrum obtained in the FT-IR measurement based on the Kubelka-Munk (KM) equation, when the peaks appearing in wavenumbers of 860 $cm^{-1}$ to 890 $cm^{-1}$ are separated, no peak near 877 cm$^{-1}$ attributed to calcium carbonate is observed. Meanwhile, the separation of the peaks is performed by processing by using, for example, a software called fityk 0.9.4 under the conditions of Function Type: Gaussian, Fitting Method: Levenberg-Marquardt.

(4) When tested according to Japanese Standards of Quasi-drug Ingredients 2006 (hydroxyapatite), the bubble generation amount is 0.25 mL or less.

<Attachment of Hydroxyapatite Fine Particles>

In the present invention, hydroxyapatite fine particles are made to be attached to a surface of the dental prosthesis or the component thereof. Here, "hydroxyapatite fine particles are made to be attached" means that hydroxyapatite fine particles are present on a surface of the dental prosthesis or the component thereof, and any method can be used. In the example of the implant, particularly, hydroxyapatite fine particles are made to be attached to a surface (in particular, the part in contact with the gingiva) of the abutment (dental material) which is a component of the implant. Here, "the part in contact with the gingiva" means a region in contact with the gingiva in use and a region expected to be in contact with the gingiva in use.

<Attachment Density>

Figure 2:
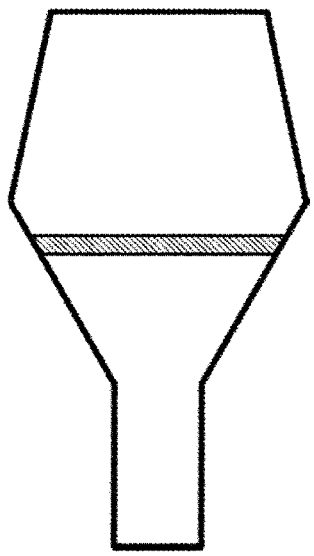
FIG. 2 is a conceptual diagram showing an abutment (dental material) in the state that sintered hydroxyapatite fine particles are provided in a ring shape around the abutment.

The attachment density (surface coverage) of the sintered hydroxyapatite fine particles on the abutment (dental material) according to the present invention is preferably 5 to 80%, more preferably 10 to 70%, and further preferably 15 to 60%. When the attachment density is within said range, it becomes possible to fill the gap parts between the abutment (dental material) and the gingiva with fibrous collagen more effectively. Meanwhile, the sintered hydroxyapatite fine particles may be partially provided around the abutment (dental material) (for example, in a ring shape as shown in FIG. 2), or may be provided throughout the abutment (dental material). Meanwhile, in the case where the sintered hydroxyapatite fine particles are partially provided, the attachment density refers to the density in a place where the sintered hydroxyapatite fine particles are provided.

The attachment density (surface coverage) is evaluated by the method described below. The surface of the material is photographed with a scanning electron microscope (SEM) at a magnification of 50,000, the obtained image is binarized with image processing software (Image J), parameters of Contrast, Noise, and Brightness are appropriately adjusted so that the silhouette of the part corresponding to the sintered hydroxyapatite particles before binarization matches to that of the part corresponding to the sintered hydroxyapatite fine particles after binarization, a substrate part and a sintered hydroxyapatite fine particle part are distinguished from each other, and the area ratio is calculated. Meanwhile, the attachment density is represented by the ratio of the area of the sintered hydroxyapatite fine particles to the total area.

<Attachment Mode>

In the abutment (dental material) according to the present invention, the mode of attachment of the sintered hydroxyapatite fine particles to the abutment (dental material) is not particularly limited, and examples include the attachment due to chemical bonding between a surface of the abutment (dental material) and the sintered hydroxyapatite fine particles, the attachment of a surface of the abutment (dental material) and the sintered hydroxyapatite fine particles by an adhesive, the embedment of the sintered hydroxyapatite fine particles into a surface of the abutment (dental material), and the like. The attachment by chemical bonding is preferable.

Depending on the degree of the strength of attachment, the above-described attachment mode is roughly classified into a drop-off type and a non-drop-off type (or a non-fixed type and a fixed type). The non-drop-off type (fixed type) means a mode in which attachment is very strong and it is expected that the sintered hydroxyapatite fine particles and the abutment (dental material) will continue to attach to each other semipermanently. On the other hand, the drop-off type (non-fixed type) means a mode in which the strength of attachment is relatively weak, and the sintered hydroxyapatite fine particles are expected to fall off from the abutment (dental material).

More specifically, when 80% or more of the sintered hydroxyapatite fine particles attached to the abutment (dental material) remain after irradiation of ultrasonic wave for cleaning (25 W, 38 kHz) for 30 minutes in comparison with before ultrasonication, attachment mode may be defined as the non-drop-off type. In other words, an attachment mode may be defined as the non-drop-off type when the percentage of the attachment density after the ultrasonication to that before the ultrasonication is 80% or more. On the other hand, those that do not satisfy this may be regarded as the drop-off type.

For example, an attachment mode by strong chemical bonding such as covalent bonding or by using a strong adhesive may be classified as the non-drop-off type. An attachment mod by weak chemical bonding such as hydrogen bonding or by using a relatively weak adhesive may be classified as the drop-off type. In addition, a attachment mode in which the sintered hydroxyapatite fine particles merely directly attach to the abutment (dental material) may be also considered to be the drop-off type. For example, such attachment mode is realized by immersing the abutment (dental material) in dispersion of the sintered hydroxyapatite fine particles and removing the solvent.

The drop-off type is particularly advantageous in the case where the substrate itself can secure a good long-term adhesion with a living body. The drop-off type is advantageous in that it attracts adhesion with tissues sintered hydroxyapatite expresses at the initial stage, and thereafter, it is possible to replace sequentially such adhesion between the living body and sintered hydroxyapatite with adhesion between the living body and the substrate. On the other hand, the non-drop-off type is advantageous in that the sintered hydroxyapatite fine particles that can favorably affect collagen production remain for a long period of time or permanently. In the present invention, the attachment mode may be either the drop-off type or the non-drop-off type, but the non-drop-off type is preferable. It is because that the non-drop-off type is thought to be advantageous for collagen production, and is conformed with the object of the present application to provide a means that makes it possible to prevent more effectively the invasion of germs from between the dental prosthesis and the gingiva and the infection and inflammation associated therewith.

<<Production Method of Abutment (Dental Material)>>

<Production Method of Sintered Hydroxyapatite Fine Particles>

The sintered hydroxyapatite according to the present invention can be produced, for example, by a method of preparing nano-size particles by using a fusion preventive agent (JP5043436B) and a method of preparing nano-size particles by pulverization (JP5781681B). Meanwhile, the nano-size sintered hydroxyapatite substantially free of calcium carbonate can be produced by a method of preparing nano-size particles by freezing before sintering (JP5980982B and JP6072967B) or a method of preparing nano-size particles by washing the sintered hydroxyapatite prepared by a method by using a fusion preventive agent (JP5043436B), with an acid (JP6072968B).

<Method of Attaching Sintered Hydroxyapatite Fine Particles to Abutment (Dental Material)>

The method of attaching the sintered hydroxyapatite fine particles to the abutment (dental material) is appropriately determined depending on the material of the abutment (dental material) and the attachment mode. Here, as described above, chemical bonding is preferable as the attachment mode.

Hereinafter, a method of attaching (a method of attaching by chemical bonding) the sintered hydroxyapatite fine particles to the abutment (dental material) material when a titanium-based material (for example, pure titanium, and a titanium alloy) is selected as the material of the abutment (dental material) will be described in detail.

(Washing Step)

The washing step of the abutment (dental material) may be carried out depending on the situation such as when contamination occurs on a surface of the abutment (dental material), and the method is not particularly limited, and examples include alkali washing and alcohol washing.

(Surface Modification Step)

The surface modification step of the abutment (dental material) is not particularly limited as long as it is the treatment by which the surface of the abutment (dental material) has a reactive group that chemically bonds with a "linker" or interacts with a "binder", used in the subsequent linker/binder introduction step. For example, in the case where the abutment (dental material) is a titanium-based material and the reactive group is a hydroxyl group, examples of surface modification include heat treatment (for example, heating under an atmosphere containing oxygen and water, usually under an air atmosphere at 150 to 500° C. for more than 0 hour and 5 hours or less), ozone water treatment (for example, see WO 2010/125686), hydrogen peroxide treatment and corona discharge treatment.

(Linker/Binder Introduction Step)

The step of introducing the linker to the abutment (dental material) is a step of making chemical bonding (covalent bonding) between the linker and the reactive group introduced on the surface of the abutment (dental material). Any compound can be used as a linker, as long as it forms covalent bonding with both the reactive group of the abutment (dental material) and the reactive group of the sintered hydroxyapatite fine particles. Since covalent bonding is known to be strong bonding, this attachment mode via covalent bonding is considered to be the non-drop-off type. When the abutment (dental material) is a titanium-based material, the hydroxyl group present on the surface of the titanium-based material may be a reactive group. Further, the hydroxyl group present on the sintered hydroxyapatite fine particles may be a reactive group. When the reactive group is a hydroxyl group, examples of the functional group reactive therewith include an isocyanate group, a carboxyl group, an alkoxysilyl group and the like. When a linker having an isocyanate group is selected, it is possible to form a urethane bond with a hydroxyl group, and when a linker having a carboxyl group is selected, an ester bond can be formed with a hydroxyl group. From these facts, when the abutment (dental material) is made of a titanium-based material, a compound having functional groups as described above can be used as a linker. More specifically, examples of a compound that can be used as a linker include a compound having two or more isocyanate groups, a compound having two or more carboxyl groups, a compound having one or more isocyanate groups and one or more carboxyl groups, a compound having one or more alkoxysilyl groups, or the like. As such a linker, a silane coupling agent is preferable.

In addition to linkers for attaching the abutment (dental material) and the sintered hydroxyapatite fine particles via covalent bonding, a compound which interacts with both the abutment (dental material) and the sintered hydroxyapatite fine particles, for example, via hydrogen bonding, may also be used. Such a compound will be referred to as a binder for convenience. By interaction of the binder with both the sintered hydroxyapatite fine particles and the abutment (dental material), the sintered hydroxyapatite fine particles can be attached to the abutment (dental material) via this binder. Since the interaction such as hydrogen bonding is relatively weak, the attachment mode by the binder is considered to be the drop-off type. Alternatively, a compound that forms covalent bonding with either of the abutment (dental material) and the sintered hydroxyapatite fine particles, and interacts with the other via hydrogen bonding or the like may be used. In this case as well, it is usually considered that the attachment mode is the drop-off type, so such a compound is also referred to as a binder.

In the case where a reactive group is a hydroxyl group and a compound having a functional group capable of reacting with a hydroxyl group (for example, a silane coupling agent) is used, firstly, the hydroxyl group on the surface of the abutment (dental material) and the above compound (for example, a silane coupling agent) react to form a bond. Next, by adding a polymerizing agent, the remaining compound (for example, a silane coupling agent) not bound to the surface of the abutment (dental material) and the compound (for example, a silane coupling agent) bound to the surface of the abutment (dental material) are polymerized to form a graft polymer. As a result, the graft polymer having a functional group (for example, an alkoxysilyl group) reactive with a hydroxyl group, is formed on the surface of the abutment (dental material), and therefore, in the immobilization treatment of the sintered hydroxyapatite fine particles described later, a functional group (for example, an alkoxysilyl group) reactive with a hydroxyl group and the sintered hydroxyapatite fine particles are bound. Here, a silane coupling agent is not particularly limited, and a silane coupling agent having a polymerizable double bond such as a vinyl-based silane coupling agent, a styryl-based silane coupling agent, a methacryloxy-based silane coupling agent, and an acryloxy-based silane coupling agent is preferred. Examples of compounds other than the silane coupling agent include hexamethylene diisocyanate, 2-methacryloyloxyethyl isocyanate, acrylic acid, methacrylic acid, 4-methacryloxyethyl trimellitate anhydride (4-META), maleic anhydride, homopolymers and copolymers of these compounds, and the like.

In addition, a compound (for example, a silane coupling agent) to be reacted with a hydroxyl group on the surface of the abutment (dental material) and a compound (for example, a silane coupling agent) to be polymerized thereafter may be the same or different.

When such a compound (for example, a silane coupling agent) is used, a hydroxyl group on the surface of the abutment (dental material) and the compound (for example, a silane coupling agent) are covalently bound to each other, and the compound (for example, a silane coupling agent) and the sintered hydroxyapatite fine particles are covalently bound to each other, and therefore, it is expected that the attachment mode is the non-drop-off type.

In the case of using a binder, for example, when the abutment (dental material) is made of a titanium-based material, firstly, intermolecular force between a polar group of the binder and a hydroxyl group or an oxygen cross-linked structure (M-O-M: metal-oxygen-metal cross-linked structure) on the surface of the abutment (dental material) is generated to cause attachment. Additionally/alternatively a polar group of the binder and the sintered hydroxyapatite fine particles are attached by intermolecular force. Here, the binder is not particularly limited, and examples of the binder include polyethylene glycol, polylactic acid, polyglycolic acid, polycaprolactone, polyvinyl alcohol, polyacrylamide, polyisopropyl acrylamide and the like. Among them, polyethylene glycol, polylactic acid, polyglycolic acid, and polycaprolactone are preferable.

In the case of using a binder, the sintered hydroxyapatite fine particles attach to the abutment (dental material) only via the interaction between the binder and at least one of the abutments (dental material) and the sintered hydroxyapatite fine particles, and therefore, it is expected that the attachment mode is the drop-off type.

(Immobilization Treatment of Sintered Hydroxyapatite Fine Particles)

The immobilization treatment of the sintered hydroxyapatite fine particles may be a step of binding the sintered hydroxyapatite fine particles to a surface of the abutment (dental material) after the linker/binder introduction step. The method of binding the abutment (dental material) to the surface of the substrate after the linker/binder introduction step is not particularly limited, and a conventionally known method may be used. For example, reference can be made to JP2004-51952A and JP2000-327314A. Specifically, the substrate may be immersed in a liquid in which the sintered hydroxyapatite fine particles are suspended. During immersion, said liquid may be stirred or ultrasonicated. Additionally, after immersion, said substrate may be allowed to stand under a reduced pressure condition, preferably under a vacuum condition, and may be further heated under a reduced pressure condition or a vacuum condition. The heating temperature is preferably 50 to 200° C., and is more preferably 80 to 150° C.

EXAMPLES

Preparation Example 1

<Preparation of Sintered Hydroxyapatite Fine Particles 1>

(Primary Particle Generating Step)

Dodecane [$CH_3(CH_2)_{10}H_3$] was used as a continuous oil phase and pentaethylene glycol dodecyl ether [$CH_3(CH_2)_{10}CH_2O(CH_2CH_2O)_4CH_2CH_2OH$] having a clouding point of 31° C. was used as a nonionic surfactant. At room temperature, 40 ml of the continuous oil phase containing 0.5 g of the nonionic surfactant was prepared. Next, 10 ml of 2.5 mol/l calcium hydroxide [$Ca(OH)_2$] aqueous dispersion was added to the continuous oil phase prepared as above to prepare a water-in-oil type solution (W/O solution). While the W/O solution was stirred, 10 ml of 1.5 mol/l potassium dihydrogenphosphate [($KH_2PO_4$)] solution was added thereto. Then, the solution was stirred at room temperature over 24 hours to cause a reaction. Next, the resulting reaction product was separated and washed by centrifugation to obtain a group of hydroxyapatite (HAp) primary particles.

(Mixing Step)

1.0 g of a group of hydroxyapatite (HAp) primary particles was dispersed in 100 ml of an aqueous solution having a pH of 12.0 and containing 1.0 g of sodium polyacrylate (manufactured by Sigma-Aldrich Co. LLC, weight-average molecular weight: 15,000 g/mol), whereby sodium polyacrylate was adsorbed on the surface the hydroxyapatite primary particles. The pH of this aqueous solution was measured by using a pH meter D-24SE manufactured by HORIBA, Ltd. Next, 100 ml of 0.12 mol/l calcium nitrate [$Ca(NO_3)_2$] aqueous solution was added to the dispersion prepared as above to deposit calcium polyacrylate on the surface of the primary particles. Calcium polyacrylate is a fusion preventive agent. The resulting precipitate was collected and dried at 80° C. under reduced pressure (about 0.1 Pa) to obtain mixed particles.

(Sintering Step)

The above-described mixed particles were placed in a crucible and sintered at a sintering temperature of 800° C. for 1 hour. At this time, calcium polyacrylate was thermally decomposed to form calcium oxide [CaO]. The residual percentage of calcium oxide [CaO] after completion of the sintering step was 25% or more.

(Removing Step)

An aqueous solution of 50 mmol/l ammonium nitrate [$NH_4NO_3$] was prepared in order to increase the solubility of the fusion preventive agent in water. Next, the sintered bodies obtained in the above step were suspended in 500 ml of the aqueous solution prepared as above, and were separated and washed by centrifugation. Further, the sintered bodies were suspended in distilled water, separated and washed by centrifugation similarly. This resulted in that the fusion preventive agent and ammonium nitrate were removed, and highly crystalline hydroxyapatite (HAp) fine particles were collected. Detailed information on the hydroxyapatite fine particles obtained by these steps is summarized below.

Half-value width of XRD: 0.519 (d=2.814)
Shape: spherical
Mean particle size (from electron microscope): 41 nm
Coefficient of variation: 18%<

>Production of Sample Material 1>

(Pretreatment)

A pure titanium material (pure titanium material of 10 mm×10 mm), which is the same material as a commercially available abutment, was heated at 300° C. for 0.5 hours.

(Surface Modification Step)

Alcohol treatment (ultrasonic irradiation in alcohol (such as ethanol, 2-propanol and the like) for 5 minutes) was performed on the pretreated pure titanium material.

(Linker Introduction Step)

In a solution composed of 3.3 ml of a silane coupling agent (γ-methacryloxypropyltriethoxysilane, manufactured by Shin-Etsu Chemical Co., Ltd., KBE 503, hereinafter simply referred to as "KBE") and 25 ml of toluene at a temperature of 70° C., the pure titanium material subjected to the surface modification treatment was immersed for 30 minutes while being bubbled with nitrogen gas. Thereafter, 5 ml of toluene in which 33 mg of AIBN was dissolved was further added, and the substrate was immersed in said solution at a temperature of 70° C. for 120 minutes while being bubbled with nitrogen gas to cause graft polymerization. Adding AIBN with a time difference in this way is for forming a graft polymer between KBE monomer bound to the surface of the substrate and free KBE in the solvent. After said treatment, in order to remove the homopolymer of KBE attached to the surface of the substrate, ultrasonic washing (50 W) was carried out in an ethanol solvent at room temperature for 2 minutes, followed by drying under reduced pressure at room temperature for 60 minutes.

(Immobilization Treatment of Sintered Hydroxyapatite Fine Particles)

Figure 3A:
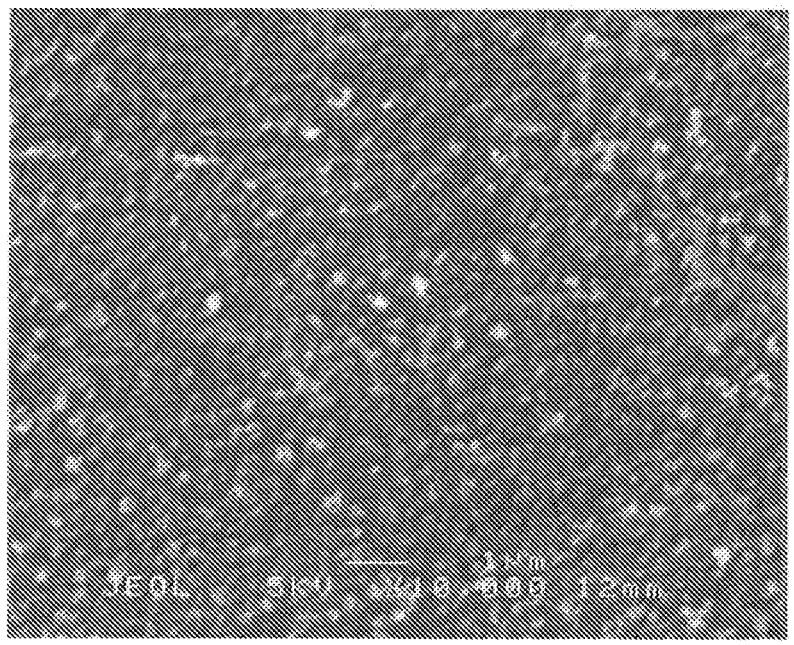
FIG. 3A is an SEM photograph of a sample material 1 according to a present example.

After the above treatment, the substrate was ultrasonicated (50 W) at 35° C. for 20 minutes in a dispersion of 1% sintered hydroxyapatite fine particles 1 (dispersion medium: ethanol). Thereafter, annealing (heat treatment) was performed at 110° C. under reduced pressure for 120 minutes. Further, ultrasonic washing (50 W) was performed on said treated substrate in ethanol at room temperature for 2 minutes to remove sintered hydroxyapatite fine particles 1 which were physically adsorbed on the surface of the substrate. Thereafter, drying under reduced pressure was performed at room temperature for 60 minutes. As a result, the sample material 1 according to the present example was obtained. Meanwhile, as can be seen from the result of the atomic analysis by X-ray photoelectron spectroscopy (XPS) shown in the following table, in the present sample material 1, it was confirmed that the pure titanium material and the sintered hydroxyapatite fine particles 1 were bound via a linker. In addition, FIG. 3A is a photograph of a scanning electron microscope (SEM) of the sample material 1 according to the present example. Meanwhile, the average coverage was 28%.

TABLE 1

| | Atomic Concentration % | | | | | |
|---|---|---|---|---|---|---|
| | Ti 2p | O 1s | C 1s | Ca 2p | P 2p | Si 2p |
| Heating at 300° C. for 30 minutes | 19.10 | 59.38 | 11.14 | 0 | 0 | 10.38 |
| KBE-503 polymer was introduced to the above | 2.71 | 27.79 | 60.19 | 0 | 0 | 9.31 |
| SHAp was immobilized on the above | 2.98 | 38.35 | 37.99 | 7.16 | 6.00 | 7.52 |

Test Example

<Evaluation of Cell Adhesion/Cell Morphology>

Figure 4:
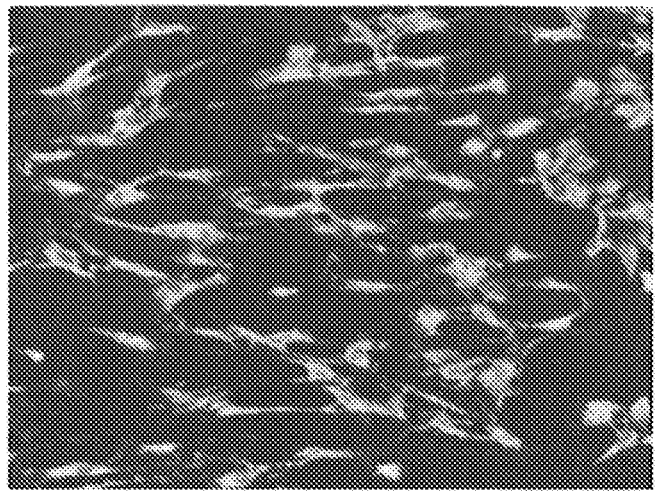
FIG. 4 is an image obtained by composing an actin-derived fluorescence image and a DNA-derived fluorescence image of the sample material 1 according to a present example.

For the sample material 1 prepared in Preparation Example 1, a cell adhesion/cell morphology evaluation test was carried out. Meanwhile, prior to the test, the sample material 1 was washed with ethanol, washed with a medium (DMEM) (3 times), soaked in the medium and incubated (37° C., 5% $CO_2$) until use. Then, cell culture was carried out according to the following procedure. First, a medium (200 μL/well) and a titanium thin film were placed in each well of a 24-well plate. Thereafter, a suspension of HGF-1 fibroblasts (P18) was placed (about $2\times10^4$ cells/500 μL/well) and the mixture was cultured for 24 hours. Subsequently, staining (for evaluation of cell adhesion/cell morphology) was carried out according to the following procedure. First, fixing treatment (4% PFA) and surfactant treatment (0.5% Triton X-100/PBS) were performed, and then, after adding Acti-stain labeled with AlexaFluor (trademark) 488, encapsulation with an encapsulating agent (containing a nuclear staining dye: DAPI) was performed. The cell morphology was observed by irradiation with a laser beam of 488 nm and staining of actin filaments. A laser beam of 405 nm was irradiated to observe the staining of cell nuclei. The result is shown in FIG. 4. FIG. 4 is an image obtained by composing an actin-derived fluorescence image and a cell nucleus-derived fluorescence image. As can be seen from said figure, when the sample material 1 according to the present example was used, it was observed that actin filaments were sufficiently developed to exhibit excellent cell adhesiveness. Moreover, it was also observed that most of the cells showed greatly expanded cell morphology.

<Evaluation of Collagen/Fibronectin Production>

Figure 5A:
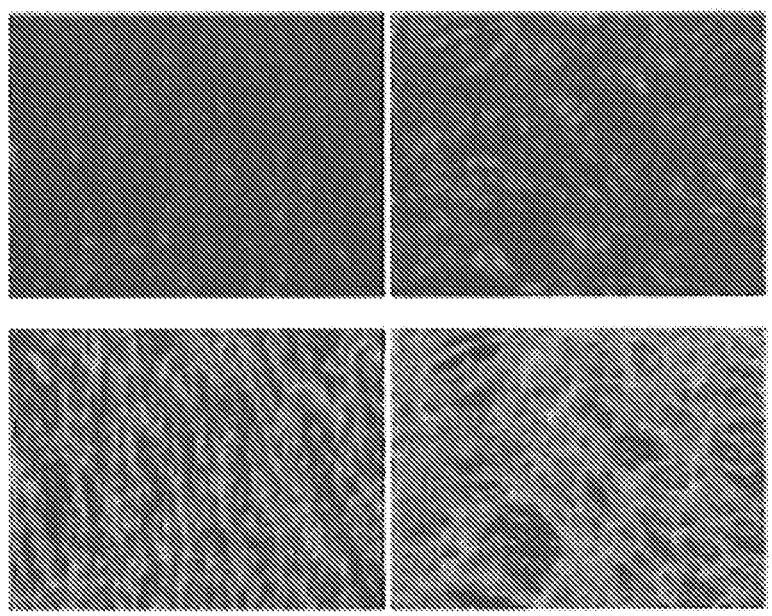
FIG. 5A shows images obtained by composing a collagen-derived fluorescence image and a DNA-derived fluorescence image (the upper left is a control and the upper right is a present example) and images obtained by composing a fibronectin-derived fluorescence image and a DNA-derived fluorescence image (the left is the control and the right is the present example) of the sample material 1 according to the present example and the control (heat-treated titanium).

A collagen/fibronectin production evaluation test was carried out on the sample material 1 prepared in Preparation Example 1. Meanwhile, prior to the test, the sample material 1 was washed with ethanol, washed with a medium (3 times), soaked in the medium and incubated (37° C., 5% $CO_2$) until use. Then, cell culture was carried out according to the following procedure. First, a medium (200 μL/well) and a titanium thin film were placed in each well of a 24-well plate. Thereafter, a suspension of HGF-1 cells (P18) was placed (about $2\times10^4$ cells/500 μL/well) and the mixture was cultured without ascorbic acid (8 days). Subsequently, staining (for evaluating collagen/fibronectin production) was carried out according to the following procedure. First, fixing treatment (methanol, −20° C.) and surfactant treatment (0.5% Triton X-100/PBS) were performed. Subsequently, biotin blocking (1% BSA/PBS→streptavidin→biotin) was performed. Thereafter, primary antibodies {biotin-labeled rat anti-type 1 collagen antibody (2 μg/mL)+rabbit anti-fibronectin antibody (1/200 dilution)} were added. Further, fluorescently labeled antibodies {AlexaFluor 555-labeled streptavidin (1/500 dilution)+AleaFluor 488-labeled anti-rabbit IgG antibody (1/500 dilution)} were added as secondary antibodies, and then encapsulation with an encapsulating agent (containing a nuclear staining dye: DAPI) was performed. Collagen was observed with 555 nm laser irradiation, and fibronectin was observed with 488 nm laser irradiation. Next, cell nuclei were observed with 405 nm laser irradiation. The result is shown in FIG. 5. The upper part of FIG. 5 shows images obtained by composing a collagen-derived fluorescence image and a cell nucleus-derived fluorescence image (the left is a control, and the right is the present example). In addition, the lower part of FIG. 5 shows images obtained by composing a fibronectin-derived fluorescence image and a cell nucleus-derived fluorescence image (the left is the control, and the right is the present example). As can be seen from said figure, when the sample material 1 according to the present example was used, it was observed that larger amounts of collagen and fibronectin were produced as compared with the control (it is understood that most of them were extracellularly formed because staining was performed after the surfactant treatment). In particular, in the case of using the sample material 1 according to the present example, collagen was produced fibrously. Since fibrous collagen was densely produced with high orientation, it is expected that produced collagen adheres to the sample material 1 according to the present example. Accordingly, for example, when the sample material 1 according to the present example is used as an abutment (dental material), produced collagen fills gaps between the abutment (dental material) and the gingiva, and it can be expected to solve the problem of the invasion of germs from said gaps and causing infection and inflammation.

Preparation Example 2

<Preparation of Sintered Hydroxyapatite Fine Particles 2>

(Primary Particle Generating Step)

Dodecane $[CH_3(CH_2)_{10}H_3]$ was used as a continuous oil phase and pentaethylene glycol dodecyl ether $[CH_3(CH_2)_{10}CH_2O(CH_2CH_2O)_4CH_2CH_2OH]$ having a clouding point of 31° C. was used as a nonionic surfactant. At room temperature, 40 ml of the continuous oil phase containing 0.5 g of the nonionic surfactant was prepared. Next, 10 ml of 2.5 mol/1 calcium hydroxide [Ca(OH)$_2$] aqueous dispersion was added to the continuous oil phase prepared as above to prepare a water-in-oil type solution (W/O solution). While the W/O solution was stirred, 10 ml of 1.5 mol/1 potassium dihydrogenphosphate [(KH$_2$PO$_4$)] solution was added thereto. Then, the solution was stirred at room temperature over 24 hours to cause a reaction. Next, the resulting reaction product was separated and washed by centrifugation to obtain a group of hydroxyapatite (HAp) primary particles.

(Freezing/Thawing Step)

Thereafter, after a supernatant in a reaction vessel was transferred to a wastewater container, deionized water was added to the reaction vessel, the mixture was stirred with a stirrer, and the supernatant was transferred to a waste container. This operation was repeated twice. Thereafter, the reaction vessel containing said precipitate was frozen as a whole at −10° C. to −15° C. overnight. After that, said precipitate in the reaction vessel was thawed at room temperature, and the precipitate after thawing was collected by filtration.

(Sintering Step)

Thereafter, sintering was carried out as follows. About 400 g of the precipitate was placed in a sintering dish, and the dish was placed in a sintering furnace, heated up to 600° C. over a period of 1 hour or more, kept at 600° C. for 1 hour, and then cooled for over 1 hour or more. Thereafter, deionized water was added to sintered bodies, and ultrasonic irradiation was performed for 30 minutes or more. Then, the sintered bodies were transferred to a pot mill, balls for pulverization were added thereto and the sintered bodies were pulverized for 1 hour. After the pulverization was finished, the sintered bodies were transferred to a beaker with handle, and the unpulverized sintered bodies were removed by using a sieve having a mesh size of 150 µm. Meanwhile, after that, washing with deionized water was repeated six times. Thereafter, the sintered bodies ware dried at 60 to 80° C. to obtain hydroxyapatite fine particles. Detailed information on the hydroxyapatite fine particles obtained by these steps is summarized below. The hydroxyapatite fine particles thus obtained all satisfied the following properties (1) to (4), and it was observed that they were substantially free of calcium carbonate.

(1) Based on the measurement result of X-ray diffraction, calcium carbonate is equal to or lower than: calcium carbonate (formula weight: 100.09)/hydroxyapatite (formula weight: 1004.62)=0.1/99.9 (formula weight conversion ratio).

(2) In the thermal gravimetric-differential thermal analysis (TG-DTA) measurement, weight loss of 2% or more with clear endothermic change is not observed at 650° C. to 800° C.

(3) In the chart showing the absorbance calculated from the spectrum obtained in the FT-IR measurement by the Kubelka-Munk (KM) equation, when the peaks appearing in wavenumbers of 860 cm$^{-1}$ to 890 cm$^{-1}$ are separated, no peak near 877 cm$^{-1}$ attributed to calcium carbonate is observed.

(4) When tested according to Japanese Standards of Quasi-drug Ingredients 2006 (hydroxyapatite), the bubble generation amount is 0.25 mL or less.

Half-value width of XRD: 0.67 (d=2.814)
Shape: spherical
Mean particle size (from electron microscope): 40 nm
Coefficient of variation: 16%<

<Production of Sample Material 2>

Figure 3B:
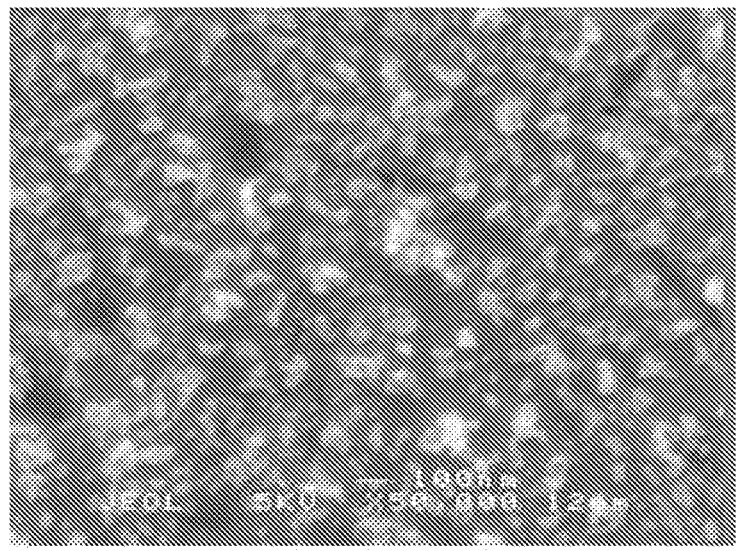
FIG. 3B is an SEM photograph of a sample material 2 according to a present example.

A sample material 2 was produced in the same manner as the sample material 1, except that sintered hydroxyapatite fine particles 1 were changed to sintered hydroxyapatite fine particles 2. Meanwhile, in the same manner as the sample material 1, in the present sample material 2, it was observed that the pure titanium material and the sintered hydroxyapatite fine particles 2 were bound via a linker. In addition, FIG. 3B is an SEM photograph of the sample material 2 according to the present example. Meanwhile, the average coverage was 32%.

Test Example

<Evaluation of Collagen/Fibronectin Production>

Figure 5B:
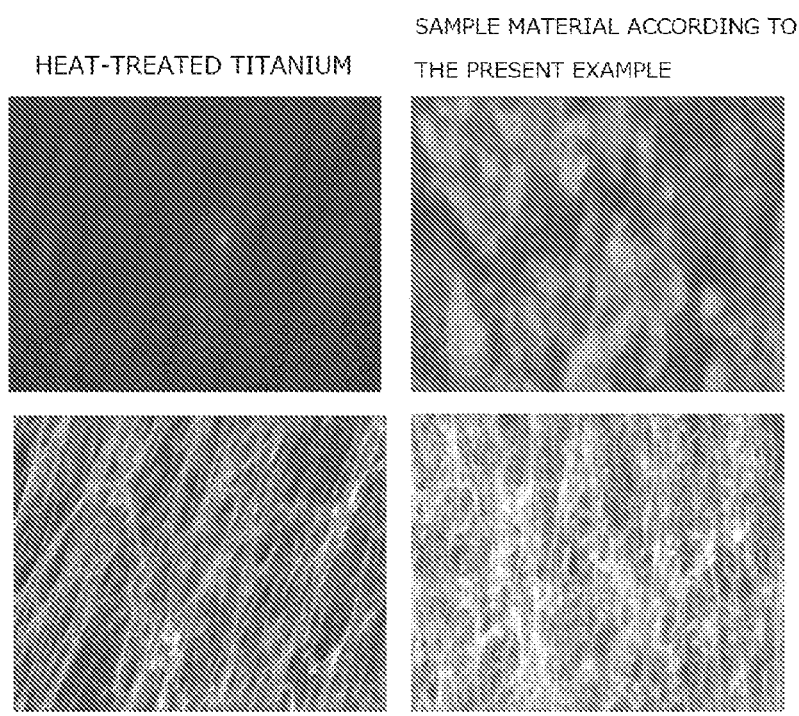
FIG. 5B shows images obtained by composing a collagen-derived fluorescence image and a DNA-derived fluorescence image (the upper left is a control and the upper right is a present example) and images obtained by composing a fibronectin-derived fluorescence image and a DNA-derived fluorescence image (the left is the control and the right is the present example) of the sample material 2 according to the present example and the control (heat-treated titanium).

The sample material 2 prepared in Preparation Example 2 was subjected to a collagen/fibronectin production evaluation test in the same manner as the sample material 1, and cell nuclei were observed in the same manner as the sample material 1. The result is shown in FIG. 5B. The upper part of FIG. 5B shows images obtained by composing a collagen-derived fluorescence image and a cell nucleus-derived fluorescence image (the left is a control, and the right is the present example). In addition, the lower part of FIG. 5B shows images obtained by composing a fibronectin-derived fluorescence image and a cell nucleus-derived fluorescence image (the left is the control, and the right is the present example). As can be seen from said figure, when the sample material 2 according to the present example was used, it was observed that larger amounts of collagen and fibronectin were produced as compared with the control (it is understood that most of them were extracellularly formed because staining was performed after the surfactant treatment). In particular, in the case of using the sample material 2 according to the present example, collagen was produced fibrously. In addition, it was observed that the amount of collagen was larger than that in Example 1 and collagen fibrosis was promoted. Since fibrous collagen was densely produced with high orientation, it is expected that produced collagen adheres to the sample material 2 according to the present example. Accordingly, for example, when the sample material 2 according to the present example is used as an abutment (dental material), produced collagen fills gaps between the abutment (dental material) and the gingiva, and it can be expected to solve the problem of the invasion of germs from said gaps and causing infection and inflammation. The sintered hydroxyapatite fine particles 2 in the sample material 2 is substantially free of calcium carbonate. Accordingly, it is possible to reduce a rapid pH change due to dissolution in a living body and a risk of inducing inflammation of the surrounding tissues accompanied therewith. Furthermore, since there is little or no loss due to dissolution, it is also advantageous in that it fills the gaps between the abutment (dental material) and the gingiva.

Further, the light absorbance at a wavelength of 450 nm of the culture supernatant was measured to calculate the collagen concentration, and the light absorbance at a wavelength of 562 nm of the culture supernatant was measured to calculate the protein concentration. From these results, the amount of collagen per the amount of protein is calculated. The amount of protein and the amount of cells are in a proportional relation, so that the amount of collagen standardized by the amount of cells is obtained. The amount of standardized collagen in the sample material 2 was 0.062. On the other hand, when the above-described commercially available pure titanium material (pure titanium material of 10 mm×10 mm) was used as it was, as well as when it was used after only being subjected to heat treatment (at 300° C.

for 0.5 hours), the amount of standardized collagen was 0.049. A significant difference in the effect of promoting collagen production was observed.

For the sample material 2 prepared in Preparation Example 2, a cell adhesion/cell morphology evaluation test was carried out in the same manner as the sample material 1. When the sample material 2 according to the present example was used, it was observed that actin filaments were sufficiently developed to exhibit excellent cell adhesiveness similarly to the sample material 1. Moreover, it was also observed that most of the cells showed greatly expanded cell morphology.

<Production of Sample Material 3>

A sample material 3 was produced in the same manner as the sample material 2, except that a binder instead of a linker caused the attachment. The steps of introducing the binder and thereafter are as follows.

(Binder Introduction Step)

A binder solution was prepared by dissolving 0.1 g of a binder (poly-L-lactic acid, manufactured by nacalai.co.jp, hereinafter simply referred to as "polylactic acid") into 10 ml of chloroform. The surface-modified pure titanium material was immersed for 30 minutes. After said treatment, in order to remove excess polylactic acid attaching to the surface of the substrate, the substrate was washed with chloroform and then dried under reduced pressure at room temperature for 60 minutes.

(Immobilization Treatment of Sintered Hydroxyapatite Fine Particles)

Figure 3C:
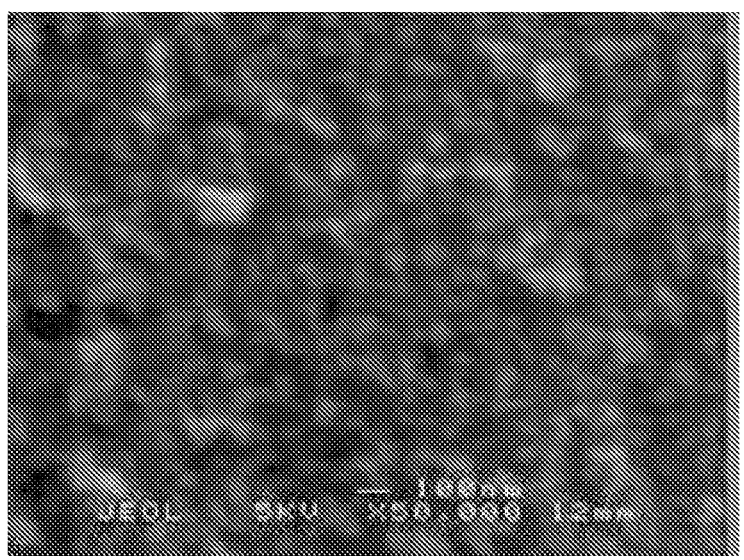
FIG. 3C is an SEM photograph of a sample material 3 according to a present example.

After the above treatment, the substrate was immersed in a dispersion of 1% sintered hydroxyapatite fine particles 2 (dispersion medium: ethanol) at 35° C. for 20 minutes. Thereafter, the treated substrate was dried under reduced pressure at room temperature for 60 minutes. Further, ultrasonic washing (50 W) was performed on said treated substrate in ethanol at room temperature for 2 minutes to remove excess sintered hydroxyapatite fine particles 2 which were adsorbed on the surface of the substrate. Thereafter, drying under reduced pressure was performed at room temperature for 60 minutes. As a result, the sample material 3 according to the present example was obtained. Meanwhile, as described later, in the same manner as the sample material 2, in the present sample material 3, it was observed that the pure titanium material and the sintered hydroxyapatite fine particles 2 were attached via a binder. In addition, FIG. 3C is an SEM photograph of the sample material 3 according to the present example. Meanwhile, the average coverage was 27%.

Test Example

<Evaluation of Collagen/Fibronectin Production>

A collagen/fibronectin production evaluation test was carried out on the sample material 3 prepared in Preparation Example 3, in the same manner as the sample material 1. When sample material 3 according to the present example was used, in the same manner as the sample material 1, it was observed that both collagen and fibronectin were produced in larger amounts as compared with a control, and in particular, collagen was produced fibrously. Since fibrous collagen was densely produced with high orientation, it is expected that produced collagen adheres to the sample material 3 according to the present example. Accordingly, for example, when the sample material 3 according to the present example is used as an abutment (dental material), produced collagen fills gaps between the abutment (dental material) and the gingiva, and it can be expected to solve the problem of the invasion of germs from said gaps and causing infection and inflammation. The sintered hydroxyapatite fine particles 2 in the sample material 3 is substantially free of calcium carbonate. Accordingly, it is possible to reduce a rapid pH change due to dissolution in a living body and a risk of inducing inflammation of the surrounding tissues accompanied therewith. Furthermore, since there is little or no loss due to dissolution, it is also advantageous in that it fills the gaps between the abutment (dental material) and the gingiva.

For the sample material 3 prepared in Preparation Example 2, a cell adhesion/cell morphology evaluation test was carried out in the same manner as the sample material 1. When the sample material 3 according to the present example was used, it was observed that actin filaments were sufficiently developed to exhibit excellent cell adhesiveness similarly to the sample material 1. Moreover, it was also observed that most of the cells showed greatly expanded cell morphology.

(Confirmation of Attachment Via Binder)

Figure 6:
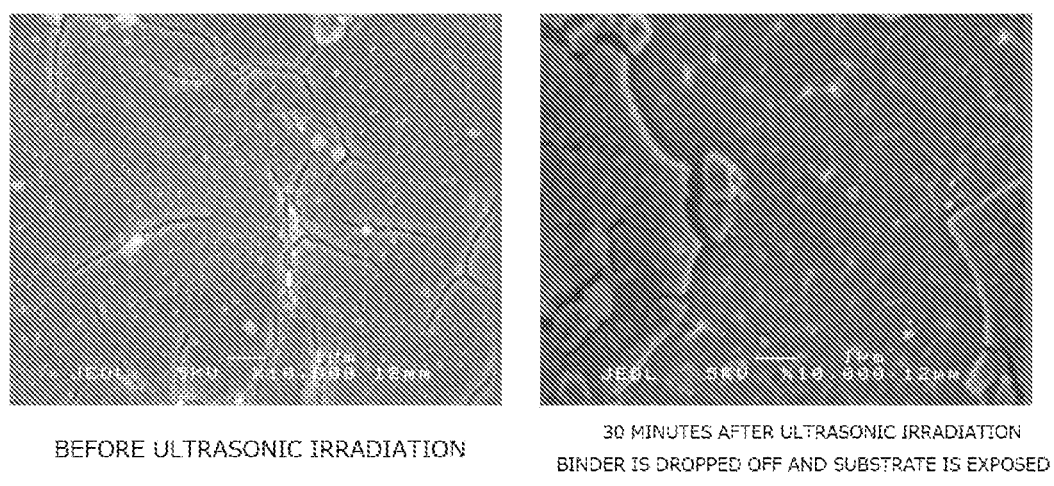
FIG. 6 shows SEM photographs of the sample material 3 according to the present example before ultrasonication and that after being subjected to ultrasonication for 30 minutes.

In order to confirm that the pure titanium material and the sintered hydroxyapatite fine particles 2 were attached via the binder, ultrasonic washing (50 W) was performed on the sample material 3 for 30 minutes at room temperature. When observing an SEM photograph of the sample material 3 at this time, it was observed that the sintered hydroxyapatite fine particles 2 were dropped off (FIG. 6). Accordingly, in the initial sample material 3, it was confirmed that the pure titanium material and the sintered hydroxyapatite fine particles 2 were attached via a binder.

The invention claimed is:

1. A method of treating a patient with at least one defect in at least one tooth, or in tissues associated with teeth, or both, comprising:
    embedding an artificial dental root in a bone in an oral cavity,
    the artificial dental root is attached to a dental prosthesis,
    the dental prosthesis comprises hydroxyapatite fine particles on a surface of the dental prosthesis,
    the hydroxyapatite fine particles are sintered bodies,
    the hydroxyapatite fine particles have a mean particle size of 10 to 1,000 nm,
    the hydroxyapatite fine particles are attached to the dental prosthesis via covalent bonding,
    the covalent bonding is formed by reacting a reactive group of the dental prosthesis, a reactive group of hydroxyapatite fine particles, and two or more reactive groups of a linker compound,
    a surface coverage of the hydroxyapatite fine particles is 15 to 60%, and
    the amount of calcium carbonate in the hydroxyapatite fine particles is equal to or lower than 0.1/99.9 of formula weight,
    wherein the surface coverage is an area ratio of a portion corresponding to the hydroxyapatite fine particles to a portion corresponding to a substrate of the prosthesis,
    wherein a weight loss of 2% or more with endothermic change is not observed in a range of 650° C. to 800° C. when measured with thermal gravimetric-differential thermal analysis, and
    wherein an absorbance plot calculated by the Kubelka-Munk equation from a spectrum obtained in a FT-IR measurement does not show a peak near 877 $cm^{-1}$ when the peaks appearing in wavenumbers of 860 $cm^{-1}$ to 890 $cm^{-1}$ are separated.

2. The method according to claim 1, wherein the linker compound is a compound having two or more isocyanate groups, a compound having two or more carboxyl groups, a compound having one or more isocyanate groups and one or more carboxyl groups or a compound having one or more alkoxysilyl groups.

3. The method according to claim 1, wherein the hydroxyapatite fine particles have a mean particle size of 20 to 300 nm.

4. The method according to claim 1, wherein a material of the dental prosthesis is a noble metal, a pure titanium, a titanium alloy, a titanium-nickel alloy, a cobalt-chromium alloy, a zirconia, an artificial sapphire, an acrylic acid, an acrylic acid derivative, a methacrylic acid, a methacrylic acid derivative, or an aromatic polyether ketone.

5. A dental component, wherein
the dental component comprises hydroxyapatite fine particles on its surface,
the hydroxyapatite fine particles are sintered bodies,
the hydroxyapatite fine particles have a mean particle size of 10 to 1,000 nm,
the hydroxyapatite fine particles are attached to the dental component via covalent bonding,
the covalent bonding is formed by reacting a reactive group of the component thereof and a reactive group of hydroxyapatite fine particles, and two or more reactive groups of a linker, and
a surface coverage of the hydroxyapatite fine particles is 15 to 60%, and the hydroxyapatite fine particles are substantially free of calcium carbonate,
the hydroxyapatite fine particles are attached to the dental prosthesis via covalent bonding,
the covalent bonding is formed by reacting a reactive group of the dental prosthesis,
a reactive group of hydroxyapatite fine particles, and two or more reactive groups of a linker compound,
the amount of calcium carbonate in the hydroxyapatite fine particles is equal to or lower than 0.1/99.9 of formula weight,
wherein the surface coverage is an area ratio of a portion corresponding to the hydroxyapatite fine particles to a portion corresponding to a substrate of the component,
wherein a weight loss of 2% or more with endothermic change is not observed in a range of 650° C. to 800° C. when measured with thermal gravimetric-differential thermal analysis, and
wherein an absorbance plot calculated by the Kubelka-Munk equation from a spectrum obtained in a FT-IR measurement does not show a peak near 877 $cm^{-1}$ when the peaks appearing in wavenumbers of 860 $cm^{-1}$ to 890 $cm^{-1}$ are separated.

6. The dental component according to claim 5, wherein the component is an abutment used for an implant.

7. The dental component according to claim 6, wherein the linker compound is a compound having two or more isocyanate groups, a compound having two or more carboxyl groups, a compound having one or more isocyanate groups and one or more carboxyl groups or a compound having one or more alkoxysilyl groups.

8. The dental component according to claim 6, wherein the hydroxyapatite fine particles have a mean particle size of 20 to 300 nm.

9. The dental component according to claim 6, wherein a material of the component thereof is a noble metal, a pure titanium, a titanium alloy, a titanium-nickel alloy, a cobalt-chromium alloy, a zirconia, an artificial sapphire, an acrylic acid, an acrylic acid derivative, a methacrylic acid, a methacrylic acid derivative, or an aromatic polyether ketone.

* * * * *